United States Patent
Gokhfeld (10) Patent No.: US 7,056,098 B2
(45) Date of Patent: Jun. 6, 2006

(54) PUMP FOR SUPPLYING A GAS TO A SENSOR AND METHODS THEREFOR

(75) Inventor: Yuzef Gokhfeld, Waltham, MA (US)

(73) Assignee: General Electric Company, Schenectady, NY (US)

(*) Notice: Subject to any disclaimer, the term of this patent is extended or adjusted under 35 U.S.C. 154(b) by 192 days.

(21) Appl. No.: 10/470,636

(22) Filed: Jan. 6, 2004

(65) Prior Publication Data

US 2005/0199037 A1    Sep. 15, 2005

Related U.S. Application Data

(63) Continuation-in-part of application No. 10/442,070, filed on May 21, 2003.

(51) Int. Cl.
*F04B 19/24*    (2006.01)

(52) U.S. Cl. ..................................... 417/207
(58) Field of Classification Search ............... 417/207
See application file for complete search history.

(56) References Cited

U.S. PATENT DOCUMENTS

| | | |
|---|---|---|
| 2,349,250 A | 5/1944 | Lloyd |
| 2,663,379 A | 12/1953 | Lloyd |
| 3,375,700 A | 4/1968 | Hubner |
| 3,687,631 A | 8/1972 | Zegel |
| 4,115,229 A | 9/1978 | Capone et al. |
| 4,169,769 A | 10/1979 | Capone |
| 5,249,929 A * | 10/1993 | Miller et al. ............... 417/207 |

FOREIGN PATENT DOCUMENTS

| | | |
|---|---|---|
| GB | 520 993 | 5/1940 |
| GB | 2 044 462 | 10/1980 |
| GB | 2 329 716 | 3/1999 |
| RU | 1170277 | 7/1985 |
| RU | 2 142 624 | 12/1999 |
| RU | 2 156 972 | 9/2000 |
| WO | 03/008928 | 1/2003 |

OTHER PUBLICATIONS

European Search Report.

* cited by examiner

*Primary Examiner*—Charles G. Freay
(74) *Attorney, Agent, or Firm*—Nixon & Vanderhye P.C.

(57) ABSTRACT

A pump for a gas sampling or analyzing system includes a pump body having walls impervious to the gas and an electrical coil within the body. The pump is coupled in series with a gas sensor and a gas volume containing the gas to be sampled or analyzed. By varying the amplitude of either the AC or DC current supplied to the coil, the temperature of the coil and, hence, the temperature of the gas within the pump can be varied, causing the pump to "inhale" upon lowering the temperature of the gas within the pump and "exhale" upon raising the temperature of the gas within the pump, thereby enabling the gas from the gas volume to be drawn periodically into and expelled from the sensor for sampling.

7 Claims, 6 Drawing Sheets

PUMP FOR SUPPLYING A GAS TO A SENSOR AND METHODS THEREFOR

RELATED APPLICATIONS

This application is a continuation-in-part of application Ser. No. 10/442,070, filed May 21, 2003, the disclosure of which is incorporated herein by reference.

BACKGROUND OF THE INVENTION

There are several known systems to detect the presence and measure the concentration of gases, e.g., combustible gases, and vapors (collectively referred to herein as "gases"). In one such system, the gases are detected based on measuring the rate of heat liberation during catalytic combustion. A combustible gas detector detects and measures combustible gases by burning a gas sample on a catalytic sensor. Catalytic combustion occurs in the sensor on a surface of a heated porous substrate, e.g. silica or alumina that has been impregnated with a catalyst. The resulting increase in temperature of the substrate is proportional to the rate of heat generation during the catalytic combustion and is measured electronically by sensing a resistance change of an imbedded resistance temperature detector (RTD). Details of other types of systems are set forth in the above-identified patent application.

In the field of gas detection/analysis, forced sampling is functionally preferred in contrast to diffusion-type sampling. In forced sampling systems, however, gas velocity variations around the sensor may provoke false sensor readings Generally, two types of pumps for gas sensors have been utilized. There are mechanical pumps which transform electrical power into mechanical movement to transmit the gas sample. Venturi-type pumps are also utilized and which pumps are more robust and reliable. However, venturi-type pumps require a high-pressure compressed air supply which may not always be available. The problem of reliability is oftentimes shifted from the pump to the air compressor. Generally, reliability and cost-effectiveness requirements cannot be met with existing gas sampling pumps, particularly in light of the requirement for ancillary equipment and the substantial number of moving parts.

BRIEF DESCRIPTION OF THE INVENTION

In accordance with an aspect of the present invention, there is provided apparatus and methods for delivering a gas sample from a controlled environment into a gas sampler or detector for determining its chemical analysis or composition which lacks moving parts, is simple in design, does not require substantial maintenance, is inexpensive, reliable and, typically, temperature and corrosion-resistant. To accomplish the foregoing, there is provided, in a system for sampling a gas having a sensor in communication with a volume of the gas, a pump for supplying a sample of the gas from the volume to the sensor; the pump including a sealed body impervious to the gas and defining a chamber in communication with the sensor and the gas volume; a heating element within the chamber of the body and a controller connected to the heating element for varying the temperature thereof and thereby controlling the temperature of the gas within the chamber to draw a sample of the gas from the volume of gas into the sensor in response to lowering the temperature of the heating element. Preferably, the heating element comprises an electric element which can be powered either from an AC or DC power source alike. The ability to choose between AC and DC power may simplify the design and reduce the cost. Additionally, the heat capacitance of the heater element is lower than the heat capacitance of walls defining the sealed body and preferably at least ten times lower. In another aspect, the controller controls the temperature to expel gas from the chamber upon raising the temperature of the gas within the chamber and draws gas into the chamber upon lowering the temperature of the gas within the chamber, with the temperature of the walls of the body defining the chamber remaining substantially constant, e.g. due to natural convection cooling, as the temperature of the gas within the chamber is raised or lowered. Increased heat capacitance of the walls vs. the heater element facilitates this requirement.

In a further aspect of the present invention, there is also provided, in a system having a sensor in communication with a volume of gas for supplying a sample of the gas to the sensor, a method including providing a sealed body impervious to the gas and having a chamber in communication with the sensor; providing a heater element within the chamber and a control for controlling the heater element to vary the temperature of the gas within the chamber; controlling the temperature of the heater element to vary the temperature of the gas within the chamber and drawing a sample of the gas from the volume into the sensor in response to lowering the temperature of the heating element. The method may also include cyclically controlling the temperature of the heater element to vary the temperature of the gas within the chamber to draw gas from the volume of gas into the sensor and expel gas from the sensor.

DETAILED DESCRIPTION OF THE INVENTION

Figure 1:
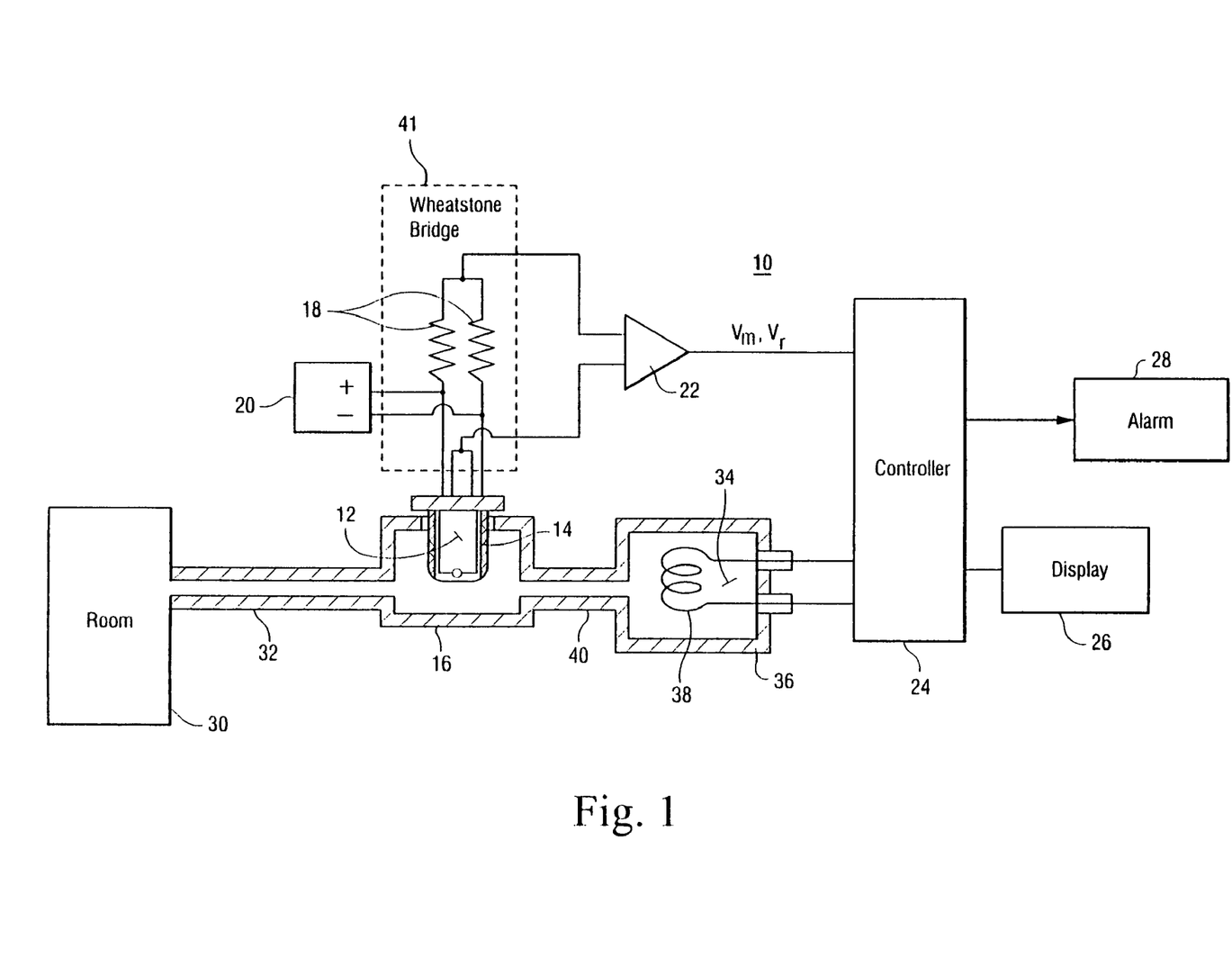
FIG. 1 is a schematic diagram showing in cross-section a gas pump in a system for sampling and analyzing a gas from a gas volume.

In FIG. 1, there is illustrated a system, generally designated 10, for sampling a gas and including a gas sensor 12 in a porous or other protective enclosure 14 and housed in a flow-through chamber 16. The chamber 16 is impervious to ambient gas diffusion and may be separated from an ambient gas volume 30 by a substantial distance, e.g. up to 10 meters. The chamber has a sample gas inlet pneumatically connected to volume 30 by a diffusion limiting passage 32, and an exhaust passage 40. The passage 32 essentially prevents the diffusion of ambient gas from the volume 30 into the chamber 16 while allowing a drawing in of a gas sample by convection or forced sampling. While the system 10, as described herein, is set forth in the context of sampling and analyzing a combustible gas, it will be appreciated that the system and particularly the pump 34 hereof is not limited to sampling and analyzing combustible gases and may be used to sample and analyze many different types of gases.

The sensor 12 in the chamber 16 may be a catalytic combustible sensor such as, for example, a conventional catalytic bead sensor having a catalytic sensing bead and a reference bead that are connected as the resistive shoulders 13 of a Wheatstone bridge 41. The bridge 41 is powered by an electrical power supply 20. The output of the bridge 41 is amplified by a pre-amplifier 22 and then is read by a microprocessor-based controller 24. The controller collects the data from the bridge output for electronic storage and processes the data to analyze whether combustible gases are present in the gas sample or evaluates the concentration and/or composition of the combustible gases based on the bridge 41 output. The controller outputs the results of its data processing to a display device 26, such as a liquid crystal display (LCD), and to a detector interface device 28, such as an alarm device.

The sensor chamber 16 is pneumatically connected to a volume 30 of the ambient gas, such as a room, stack, or other volume potentially having gases to be sampled. The chamber is isolated from ambient gases so that the gases are prevented from reaching the sensor 12 by diffusion from the volume 30. The diffusion preventing passage 32 connects the chamber 16 to the gas volume 30. The passage 32 may be a tube having an inside diameter of 0.1 mm to 3 mm and a length of 10 mm to 10,000 mm. More specifically, the dimensions of the passage 32 are chosen to reduce the rate of ambient gas diffusion through the passage to be less than a convection flow rate forced by the sampling pump 34 hereof. The passage 32 virtually prevents the diffusion of combustible gases from the outside volume 30. Preventing diffusion gas flow into the chamber 16 facilitates the process of temporarily removing combustibles from the gas sample when the sensor is being zeroed. Passage 32, which minimizes diffusion gas flow, may also serve as a flame arrestor to prevent flashback of flames in the sensor chamber 16. Gas samples flow essentially by convection from the volume 30, through the passage 32 and into the sensor chamber 16. The passage 32 also effectively isolates the chamber 16 from variations in the flow of ambient gas in the volume 30, while providing a conduit for samples of ambient gas to be drawn into the chamber 16.

The volume 30, passage 32, and sensor chamber 16 of the detector are pneumatically connected in series to a gas pump 34. The pump 34 draws a controlled flow of sample gas from the volume 30, through the passage 32, and into the sensor chamber 16. The pump is preferably a "breathing" pump that responds to control signals from the controller 24. The breathing pump 34 may be a sealed pump chamber 36 that houses a heater coil 38 controlled by the controller 24. By cyclically heating and cooling the gas in the chamber 36, gas is pumped out of and drawn into the pump chamber 36. Breathing pump 34 is mechanically simple, works reliably, and has longevity. Breathing pump 34 has no moving parts and may operate at ambient temperatures up to about 500° C.

The flow of sample into the chamber 16 is preferably interrupted while the sample is burned and measured. Interruption of the sample gas flow can be achieved by controlling the pump 34. The pump 34 "inhales" a small controlled volume of gas (sample gas), and then purges ("exhale") the sample in a repeating cycle.

The heater coil 38 may be formed from supported 12.5-micron (0.0005 inch) thin stainless steel foil which is inexpensive and readily available on the market. In this case the time of the heater to heat up or cool down to a constant temperature will be typically from less than a second to a few seconds. By way of example, the sensor chamber 16 volume may be between 1 cc (cubic centimeter) and 10 cc, and the pump chamber 36 volume may be from 5 cc to 200 cc. The volumes of the sensor and pump chambers may vary with specific design applications of the gas detector.

A diffusion preventing pump passage 40 provides a fluid connection between the pump chamber 36 and sensor chamber 16. The pump passage 40 may be formed of a tubing material that is the same or similar to the passage 32. The dimensions of the pump passage 40 and passage 32 are preferably selected so that the rate of gas diffusion through the passage 32 and pump passage 40 is lower than the average pumping flow rate. As an example, a diffusion rate of hydrogen through a 1 mm inside diameter (ID) tube with 500 mm length at normal conditions will be close to 0.0001 $cm^3/sec$. This flow rate is sufficiently small when compared with the typical 0.1 $cm^3/sec$ of the averaged rate of gas sampling into the sensor chamber by convection. The diffusion rates of gases other than $H_2$ are even lower. In practice, a non-zero diffusion rate will introduce a measurement error so insignificant, that this is usually not a problem. Obviously, the diffusion can be further reduced or zeroed by employing a known mechanical shut-off device such as e.g. solenoid valves.

Figure 2:
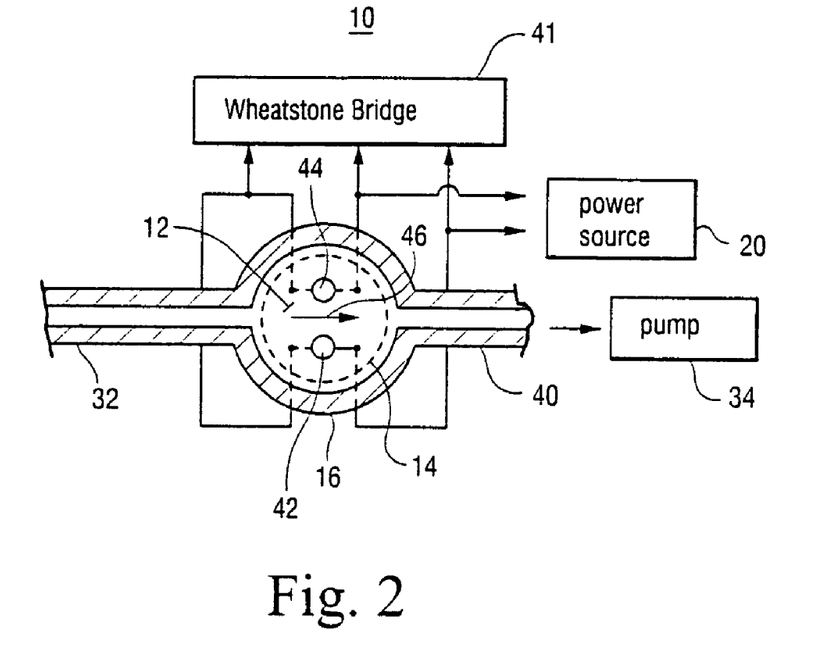
FIG. 2 is a schematic diagram showing in cross-section flow-through enclosure for a catalytic bead and reference bead of a combustible gas detector in the system shown in FIG. 1.

FIG. 2 is a schematic top-down, cross-sectional view of a part of the detector 10, including the sensor 12, enclosure 14 and chamber 16. The catalytic sensing bead 42 and reference bead 44 are preferably arranged symmetrically in the enclosure 14 and chamber 16. The beads 42 and 44 are arranged symmetrically with respect to the gas flow 46 passing through the enclosure 16. For example, the beads may be equidistant from each other on opposite sides of the axis of the flow path 46 through the chamber 16. The beads are aligned in the flow path such that both beads are exposed to substantially the same flow conditions at substantially the same time, while being spatially offset from each other in the sensor enclosure 14. Because the beads have similar gas exposure conditions, the response of the sensing bead and reference bead to gas flow should be the same, except for the burning of combustible gases on the sensing bead 42.

The symmetric alignment of the beads 42, 44 with respect to each other in the flow path 46 should minimize any "offset" sensor signal when there are no combustible gases in the sample gas flow. It was found by experiment that a balanced positioning of the beads minimizes the offset to the equivalent of less than 20 ppm of combustible gases in a gas sample at typical flow rates through the chamber 16 of up to several cubic centimeters per second. If the beads are not symmetrically arranged, the offset sensor signal may be significant. Such large offset sensor signals are common in conventional sensors because the catalytic sensing bead and reference bead are positioned in the flow path which tends to change direction and rate randomly. The RTDs of the beads will respond non-symmetrically, for example, when one bead is upstream of the other bead or the beads do not see substantially the same flow conditions of the gas sample.

Figure 3:
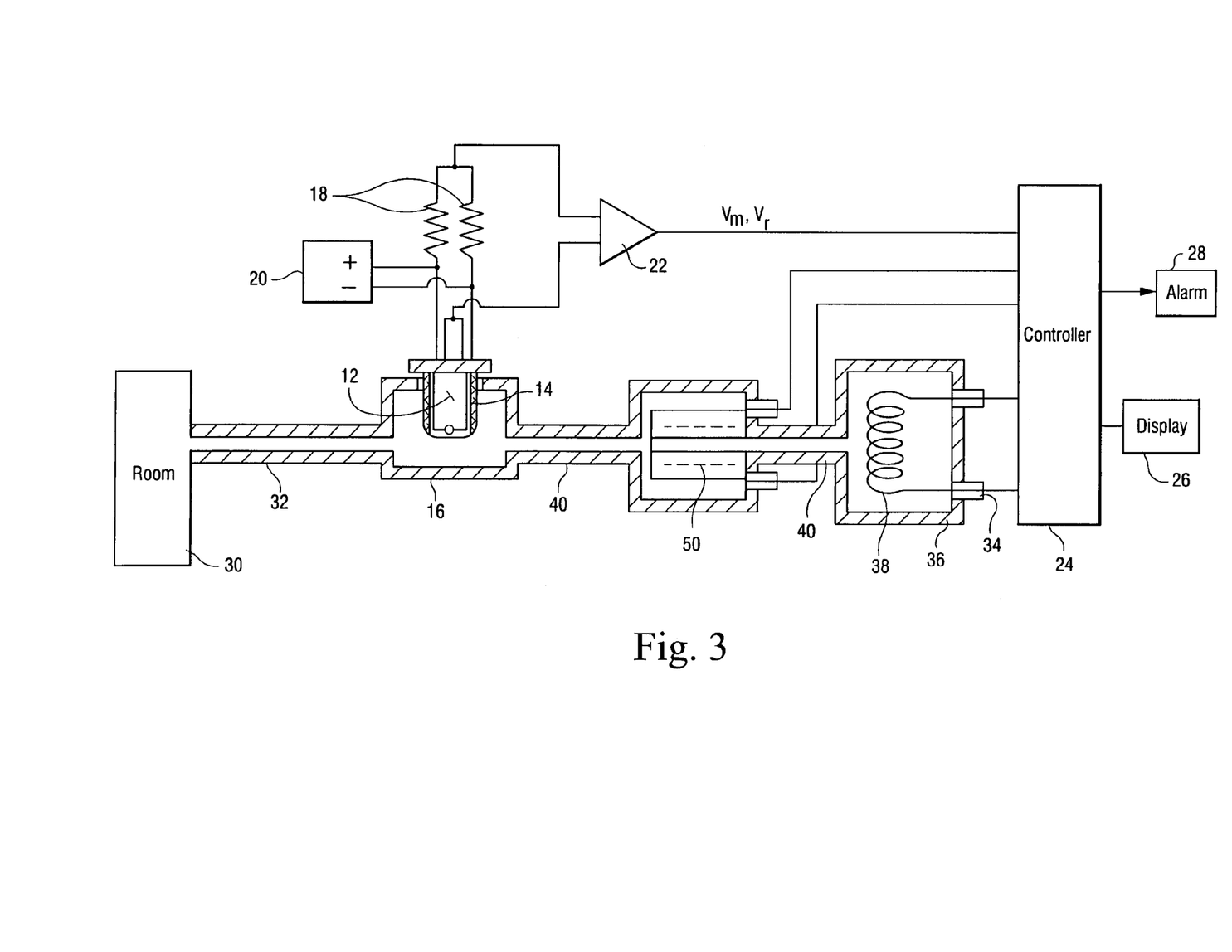
FIG. 3 is a schematic diagram showing in cross-section a second embodiment of the system.

As shown in FIG. 3, the detector 10 may also include a "blow-through" current-controlled electrolyzer 50 positioned in the pump passage 40. The electrolyzer is pneumatically connected between the sensor chamber 16 and the pump 34. The electrolyzer is designed for generating hydrogen gas (and oxygen) when electrical current passes through its matrix capable to absorb ambient moisture from the gas flowing through the pump passage 40. A suitable fast response electrolyzer is known and shown in USSR Patent No. 1170277.

The gas sample flow rate into the sensor chamber, while being relatively low to minimize flow error, exhibits rapid relative changes from zero to maximum, usually in a few seconds time. The gas sampling is interrupted, e.g., for periods of 5 to 30 seconds to zero the sensor. Accordingly, a gas mixture from outside is sampled into the sensor chamber 16 not constantly, but by relatively small portions. Combustible gas(es) in each sample portion is allowed to burn (and raise the temperature of the sensing bead), preferably until the burn-out of combustible gases in the sample is essentially completed, and only then the gas portion in the chamber 16 is replaced. It will be appreciated that gas flow in and out of the "breathing" pump 34 occurs only when the coil temperature changes. When the pump heating coil remains at a constant temperature (e.g. while heated constantly), the "breathing" stops and flow of the gas through the chamber 16 remains practically zero. In other words, intermittent and relatively short (e.g. 1-second) "inhale" and "exhale" bursts are divided with a longer (e.g. 15-second) pause.

Figure 4:
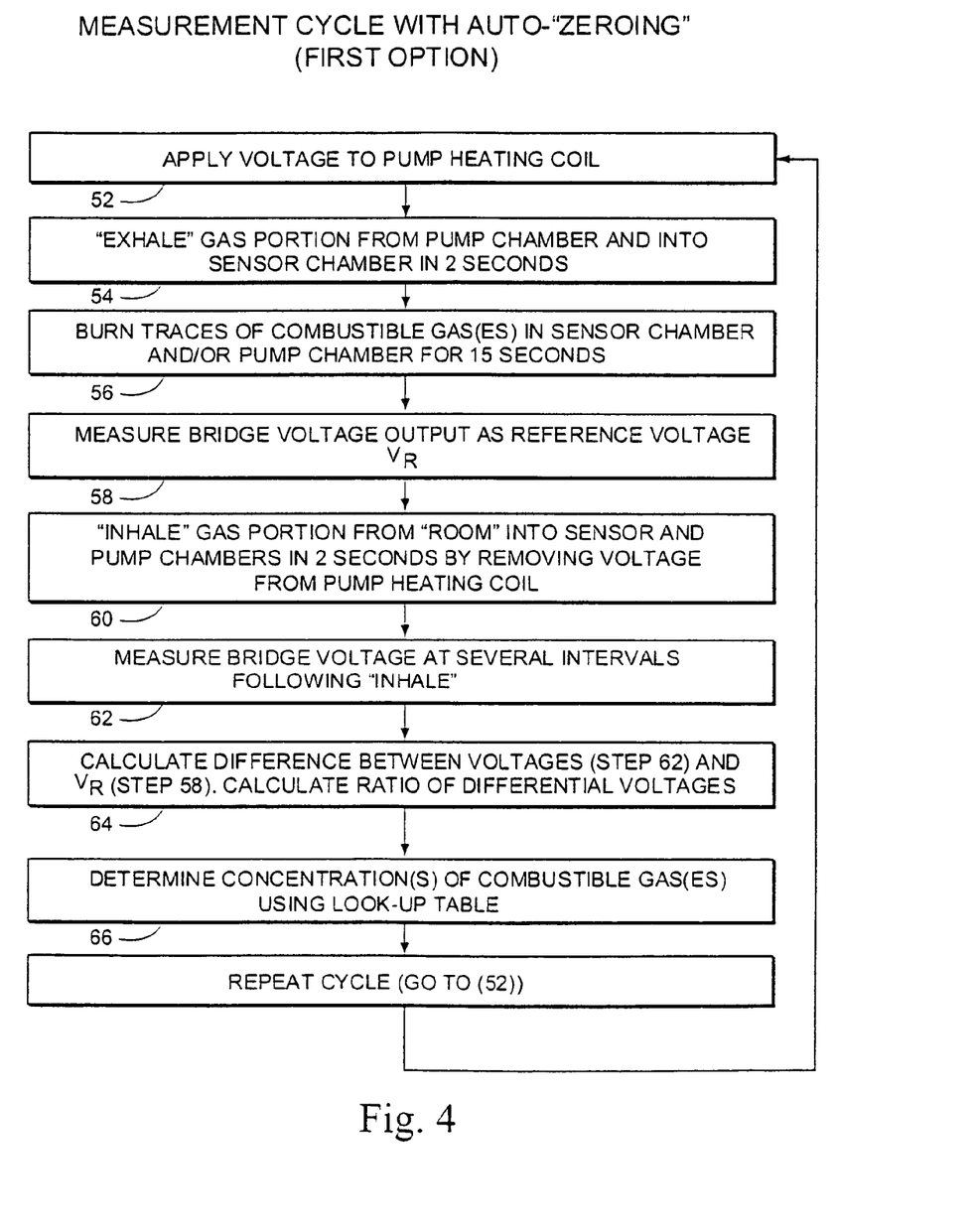
FIGS. 4 to 6 are flow charts of a gas sampling and calibration processes.
Figure 5:
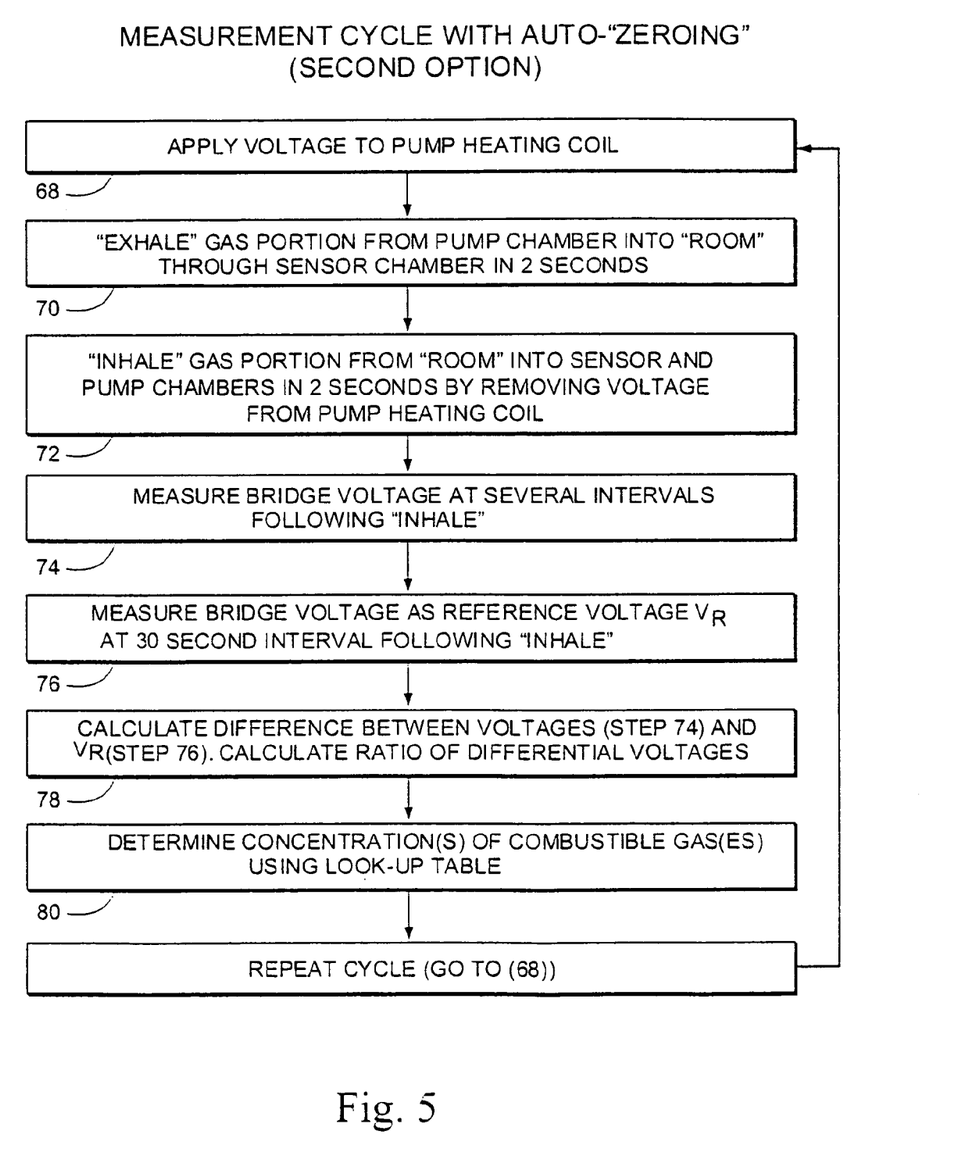
Figure 6:
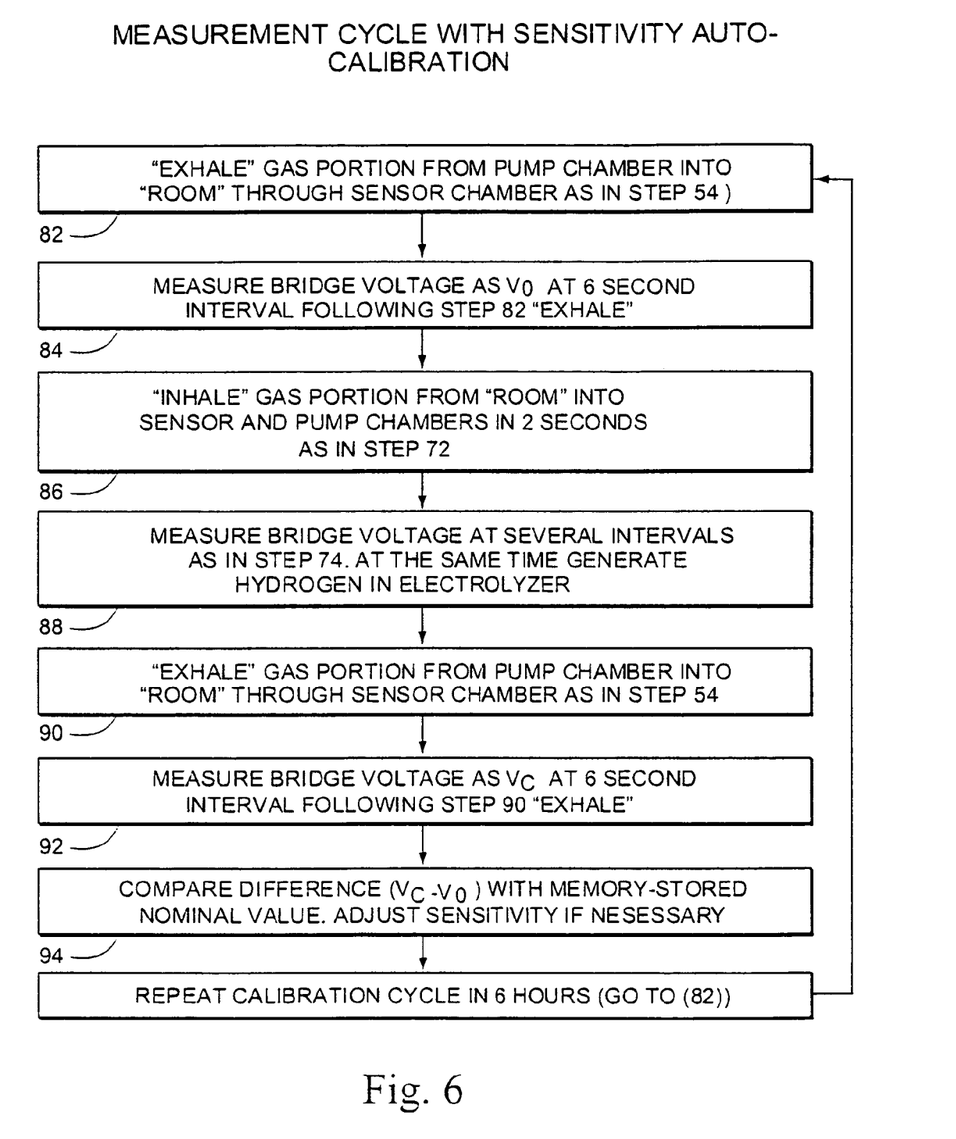

FIGS. 4 to 6 are process charts of exemplary steps of operating the detector 10. FIGS. 4 and 5 show alternative combustible measurement cycles, each with automatic zeroing ($V_r$) steps. FIG. 6 shows a calibration process to check whether a detector is poisoned. The gas detector 10 may be electrically powered, e.g. by 3 Watts, to heat up the "breathing" pump heater coil 38 in step 52,68. The controller 24 may power the coil 38 for a fixed period of time. When powered, the temperature of the heater coil rises within a few seconds, to between 100° C. and 200° C. above ambient temperature, for example. While the coil heats the gas inside the pump chamber 36, the heated gas pushes itself out through the pump passage 40, sensor chamber 16, passage 32, and into the volume 30 to purge the detector 10, in step 54. During and especially after this purge period (when gas flow for some time remains virtually zero), combustible gases that may be present in the pump and/or passage 40 would flow into the sensor chamber 16 and burn out on the sensor catalyst bead 42 and/or on the heater 38, in step 56. The reference voltage measurement process may be performed just before sampling a gas (see FIG. 4) or after sampling (see FIG. 5).

A technique to expedite the burn out of combustible gases during the purge step, in the sensor chamber, is to burn gases in the pump chamber, in step 56. For example, a thin layer of Pt may be applied to the heater coil 38 to promote catalytic combustion. When the coil 38 is heated, combustible gases in the pump chamber 36 are substantially burned out before they can flow through the pump passage 40 and into the sensor chamber 16.

After the gas flow into the chamber 16 has been interrupted and the sensor 12 burns down combustible gases already in the sensor chamber 16, in step 56, the output of the Wheatstone bridge is measured, in step 58. The measurement is digitally stored in the controller memory for future use as the reference voltage $V_r$. "Reference voltage" ($V_r$) may be defined as the "zero combustibles" bridge voltage output after the gas flow into the chamber 16 has been interrupted and the combustibles in the chamber are essentially completely burned out. Alternatively, the reference voltage may be measured after the gas has initially been sampled. The conditions suitable for the reference voltage $V_r$ to be accurately measured in this case are achieved in about 30 second or more time interval after the gas sample flow has been interrupted (end of the "inhale"), in step 76.

The controller 24 turns off the heater 38, and allows the thin-film heater coil 38 to cool, which typically takes about one to three seconds. While the heater 38 and the gas in the pump chamber cool down, the pump inhales a portion of the sample gas from the room 30, in steps 60,72. The pump inhales a known and fixed (usually small) sample of gas from the room volume 30, through the diffusion-limiting passage 32 and into the sensor chamber 16.

Combustible gases in the inhaled gas sample burn on the catalyzed sensing bead 42, in steps 62, 74. Optionally, the gas sample is allowed to stay in the chamber 16 until the combustibles burn out virtually completely (usually for about 30 seconds). At this time, the sensor output is measured as the reference voltage $V_r$, in step 76.

During the pump "inhale," i.e., when the heater coil 38 cools and cools the gases in the pump chamber, a gas sample is quickly drawn into the sensor chamber in a controlled amount. As the combustibles in the gas sample burn, the temperature of the sensing bead 42 temporarily rises and causes a change in the bead resistance. The temperature rise of the sensing bead causes the Wheatstone bridge to produce a bridge output voltage $V_m$ that is indicative of the sensing bead temperature. The bridge output voltage is measured at one or more gas sample measurement times, in step 62.

The controller detects the combustible gas concentration in the sampled gas by determining the difference between $V_r$ and $V_m$ for one or more sample measurement times, after the gas sample is "inhaled" by the pump, in steps 64, 78. This differential series of voltage measurements allows the controller to generate accurate and precise readings of the combustible gas(es) concentration in the sampled gas for a long period of time (i.e. for several years without manual calibration) by using a memory-stored look-up table, as in steps 66,80. The look-up table converts the differential voltage measurement to a combustion temperature of the sample gas.

The variations in the ambient background gas are compensated for by frequent zeroing of the sensor and, do not affect the differential sensor measurement of the combustible gas(es) concentration.

The catalytic sensor bead temperature will increase and then decrease as the "inhaled" sample with combustible gases burns and until it burns out virtually completely in the chamber 16. Based on experiments conducted of an embodiment of the detector 10, dynamic characteristic of the bridge output depends on the type of combustible gas and/or the ratio of two or more combustible gases concentrations simultaneously present in the sample. For instance, a maximum rate of burning and consequent maximum bridge output voltage will be achieved in about five seconds after the "inhale" of gas sample with hydrogen only as a combustible, and in about nine second with CO only. This data is based on a gas sample "inhale" time of less than two seconds. In $H_2$/CO gas mixtures, the maximum rate of burning (indicative by maximum bridge output voltage) gradually shifts during the five to nine second interval, with the relative increase of CO concentration vs. $H_2$ in the mixture. The rate of temperature increase in the sensor 12 due to a fast introduction of new gas sample into the chamber 16 is indicative of the composition of combustible gases mixture. The rate of temperature increase of the sensing bead can be determined, e.g., by measuring the Wheatstone bridge output at several time intervals following the "inhale" period. The rate at which the combustible gases burn depends on the diffusion coefficient of the specific combustible gas in the sample and on the catalyst temperature. Otherwise, the amplitude of the temperature increase of the sensing bead 42 is proportional to the concentration of combustible gas(es) in a range from the lower sensor detection limit to several percent of combustible gas concentration.

In general, a change in amplitude and rate of heating of the sensing bead due to different compositions of the combustible gases can be analyzed by having the controller 24 identify the type and concentration(s) of combustible gas(es,) or evaluate the ratio between two combustible gases in a gas sample drawn into the sensor enclosure 16 from the room volume 30.

It was found experimentally, that a simplified algorithm might be used to determine the ratio between $H_2$ and CO concentrations as well as the concentration of the sum of these gases with practically sufficient accuracy. For this purpose, three Wheatstone bridge outputs $V_5$, $V_{12}$, and $V_r$ are measured at three different time intervals, respectively, following the gas sample "inhale". The time intervals (delays) between the start of "inhale" (which duration is about one second) and voltage measurements are 5 seconds, 12 seconds, and 30 seconds for $V_5$, $V_{12}$, and $V_r$, respectively. The difference $V_{12}-V_r$ was found to represent the sum of CO and H2 concentrations (independently from their ratio in the sample gas) and can be used to determine the concentration of CO and $H_2$ combustibles by having the controller 24 use a look-up table. The ratio $(V_5-V_r)/(V_{12}-V_r)$ is generally in a range of 0.9 to 1.7 and practically linearly depends on the CO/H2 ratio, with the ratio of 0.9 corresponding to 100% CO and the ratio 1.7 corresponding to 100% $H_2$. The timing and/or $(V_5-V_r)/(V_{12}-V_r)$ ratio equivalent may be specific to a specific sensor type and sensor chamber geometry. Generally, it may require a preliminary calibration. By determining $(V_5-V_r)/(V_{12}-V_r)$, the concentrations of CO and $H_2$ can be determined for each gas. Thus, the individual and combined concentration levels of CO and $H_2$ can be determined from a single measurement cycle and at the same temperature of the sensor beads. The differential voltages $(V_5-V_r)$ and $(V_{12}-V_r)$ are measured in step 64. In step 66, the total concentration of CO and $H_2$ (individually and in sum) may be found by the controller using comparing the CO to $H_2$ ratio look-up table, and performing a linear approximation.

To determine the concentrations of CO and $H_2$ separately and with relatively high accuracy, a measurement cycle of one minute or longer may be required. A significantly shorter measurement cycle may be used if the composition of the gas sample with respect to combustible gas(es) is known and the sum of combustible gases is the only interest. Alternatively, shorter and longer measurement cycles can be alternated with a software initiated switch in the controller. For example, by using a "long" measurement cycle the controller can initially measure CO/H2 ratio once in a given process. The controller may subsequently automatically apply a "fast" measurement cycle(s) that assumes that the measured CO/$H_2$ ratio is a constant known quantity (as measured at the last long cycle). Periodically, the controller may perform a long cycle to re-measure CO/$H_2$ ratio.

With relatively short time intervals between gas samplings ("inhales") the combined concentration of combustibles can be determined by measuring the difference between maximal and minimal values of the sensor output within measurement cycle, which is in practice the alternating part of a full sensor signal.

The detector automatically performs a "zero" auto-calibration after each measurement cycle, in step 66. The auto-zeroing method enables the detector to accurately measure small amounts of combustibles in a sample gas by detecting changes in the temperature of the sensing bead within measurement cycle down to about 0.002° C. Auto zeroing may be performed by measuring the reference sensor output ($V_r$) either at the end of the "inhale" step, as in step 76, or just before the end of the "exhale" step, step 58.

During the measurement cycle the detector may "inhale" a small gas sample, e.g., 0.1 cc to 1 cc, into the sensor chamber 16. As the chamber may have a volume of about 2 cc, the small gas sample becomes diluted (when entering the chamber having a chamber volume substantially larger than the gas sample). In experiments, the detector reliably measured "external" $H_2$ concentration up to 8% of hydrogen (2 LEL) in air.

Auto-calibration of sensitivity may be performed periodically, e.g., once every several minutes to once every several hours. When an ambient moisture type electrolyzer is used, a re-calibration cycle time is limited by replenishing the electrolyzed water back from sample gas. Typically, the 5 $mm^3$ to 10 $mm^3$ of $H_2$, needed for a single calibration is replenished by ambient moisture ideally in about 20 minutes even at a −30° C. Dew (Frost) Point (DP) condition. The higher the DP, the faster the replenishment by ambient moisture. In reality, it may take more than an hour to replenish, especially for a low DP gas sample. The moisture limitation is not an issue with regards to flue gas analysis, because DP temperature of flue gases is usually close to +50° C. It should be noted, that presence of hydrogen or hydrocarbons in air even well below LEL would generate significant amount of moisture due to combustion on the sensor.

As shown in FIG. 6, sensitivity calibration starts at a regular (first) pump "exhale" of residual gas portion through the chamber 16 and further outside into the room, as in step 82. The sensor output ($V_0$) is measured with a pre-determined time delay after the start of "exhale" (Step 84). After the regular "inhale" (step 86) but before the beginning of the next (second) "exhale" step, a pre-determined amount of electricity passes through the electrolyzer 50 to generate a fixed amount of hydrogen inside the enclosure 51 of the electrolyzer, in step 88. For this purpose the electrolyzer is powered by a fixed current, e.g. in the range from 1 mA to 10 mA, and over a fixed period of time, e.g. from 1 to 10 seconds. This period for generating hydrogen should be preferably less than period between the pump "exhale" and "inhale" steps during regular sample gas measurements. A relatively small amount of hydrogen generated, e.g. from 0.1 $mm^3$ to 10 $mm^3$, is usually sufficient for the calibration.

The pump "exhales" for the second time in step 90. The gas portion carried over from the pump through the electrolyzer chamber 51 and into the chamber 16 during the second "exhale" contains a fixed amount of hydrogen generated in the electrolyzer. The sensor output ($V_c$) is measured, in step 92, during the burning of hydrogen and preferably with the same time delay from the start of the second "exhale", as $V_O$ after the start of the first "exhale". This delay time is usually in the range of 2 seconds to 10 seconds with the most optimal value corresponding to the time of maximum combustion rate of hydrogen introduced as a sample into the sensor chamber, typically close to 6 seconds. Due to the controlled (fixed) amount of the gas "exhaled" and the repeatable amount of hydrogen generated, the calibration process can be repeated, e.g. every few hours, with sufficiently high accuracy and repeatability within the extended period of time, e.g. for several years. The electrolyzer may not require manual service for years, as the electrolyzed water is replenished from the environment.

The difference between $V_c$ and $V_0$ is evaluated by the controller 24 and compared with a memory-stored acceptable range for this difference, in step 94. If the sensor is sufficiently sensitive, then the difference between $V_c$ and $V_0$ will be within the predetermined range. Based on the $V_c-V_o$ comparison, in step 94, a decision or automatic action concerning the sensitivity of the sensor and sensor adjustment is made. $V_0$ and $V_c$ may be measured ether as differential signals with respect to $V_r$ or as absolute values. Anyway, $V_r$ is cancelled out during the subtraction of $V_0$ from $V_c$.

With the zero sensing method shown in FIG. 6, sensor poisoning may be quickly detected by automatic calibration after each calibration cycle. As sensitivity calibration is performed during the "exhale" phase of the measurement cycle, the calibration is virtually transparent to the detector user, and does not interfere with or interrupt the regular LEL measurements. Relatively small amount or oxygen generated in parallel with hydrogen does not affect the sensor calibration accuracy, as a significantly larger amount of $O_2$ usually is already present in the gas sample.

The detector 10 disclosed herein may include features and functions such as: a transparent automatic "zeroing" between each measurement to improve long-term stability and minimize calibration requirements; reduced exposure of the sensing beads to gas samples that may contain sensor poisoning components; measurements of CO and $H_2$ concentrations separately, which may have particular application in flue gas analysis; measurements of the concentration of combustible gases at levels of detectivity down to ±10-ppm (parts per million); measurement of combustibles in high ambient gas flow rate applications such as inside a gas turbine enclosure; a sensor can be remotely located, up to several meters, from a sampling point; automatically monitoring and adjustment of sensor sensitivity while the sensor is on-line; reliable measurements of the concentration of combustibles significantly above LEL levels with fast sensor recovery for subsequent measurements.

Zero and sensitivity calibrations, as described herein, may both be employed as auxiliary and relatively infrequent (e.g. once in several hours) procedures in a sensor with otherwise uninterrupted gas sampling and a known standard bridge output measurement to fulfill the requirements of LEL detector fast speed of response.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In a system for sampling a gas having a sensor in communication with a volume of the gas and a pump for supplying a sample of the gas from the gas volume to the sensor, said pump including a sealed body impervious to the gas and defining a chamber in communication with the sensor and the gas volume, a heating element within the chamber of the body and a controller connected to said heating element for varying the temperature thereof and thereby control the temperature of the gas within said chamber to draw a sample of the gas from the volume of gas into the sensor in response to lowering the temperature of the heating element, the heat capacitance of the heater element being lower than the heat capacitance of walls defining the sealed body.

2. A system according to claim 1 wherein said controller cyclically raises and lowers the temperature of the gas within the chamber to expel gas from and draw gas into the chamber, respectively, with an interruption in the change of temperature of the gas after the gas temperature is lowered to cease movement of the gas into the chamber.

3. In a system for sampling a gas having a sensor in communication with a volume of the gas and a pump for supplying a sample of the gas from the gas volume to the sensor, said pump including a sealed body impervious to the gas and defining a chamber in communication with the sensor and the gas volume, a heating element within the chamber of the body and a controller connected to said heating element for varying the temperature thereof and thereby control the temperature of the gas within said chamber to draw a sample of the gas from the volume of gas into the sensor in response to lowering the temperature of the heating element, the heat capacitance of the heater element being at least ten times lower than the heat capacitance of the walls defining the sealed body.

4. In a system for sampling a gas having a sensor in communication with a volume of the gas and a pump for supplying a sample of the gas from the gas volume to the sensor, said pump including a sealed body impervious to the gas and defining a chamber in communication with the sensor and the gas volume, a heating element within the chamber of the body and a controller connected to said heating element for varying the temperature thereof and thereby control the temperature of the gas within said chamber to draw a sample of the gas from the volume of gas into the sensor in response to lowering the temperature of the heating element, the controller controlling the temperature of the gas within the chamber to expel gas from the chamber upon raising the temperature of the gas within the chamber and to draw gas into the chamber upon lowering the temperature of the gas within the chamber, walls of the sealed body having a heat capacitance such that the temperature of the walls remains substantially constant as the temperature of the gas within the chamber is raised or lowered.

5. A system according to claim 4 wherein said heating element is an electric element.

6. A system according to claim 2 wherein said controller includes an AC power source.

7. In a system for sampling a gas having a sensor in communication with a volume of the gas and a pump for supplying a sample of the gas from the gas volume to the sensor, said pump including a sealed body impervious to the gas and defining a chamber in communication with the sensor and the gas volume, a heating element within the chamber of the body and a controller connected to said heating element for varying the temperature thereof and thereby control the temperature of the gas within said chamber to draw a sample of the gas from the volume of gas into the sensor in response to lowering the temperature of the heating element, said heating element being an electric element, the heater element comprising a foil of about 12.5 microns or less thick.

* * * * *

UNITED STATES PATENT AND TRADEMARK OFFICE
CERTIFICATE OF CORRECTION

PATENT NO. : 7,056,098 B2
APPLICATION NO. : 10/470636
DATED : June 6, 2006
INVENTOR(S) : Gokhfeld It is certified that error appears in the above-identified patent and that said Letters Patent is hereby corrected as shown below:

At column 3 line 5 the numeral "13" should read "18"

Signed and Sealed this

Third Day of October, 2006

JON W. DUDAS
*Director of the United States Patent and Trademark Office*